United States Patent [19]

Durant et al.

[11] 4,093,729

[45] June 6, 1978

[54] N-OXY AND N-AMINO GUANIDINES

[75] Inventors: Graham John Durant; Charon Robin Ganellin; Geoffrey Robert Owen, all of Welwyn Garden City, England

[73] Assignee: Smith Kline & French Laboratories Limited, Welwyn Garden City, England

[21] Appl. No.: 786,729

[22] Filed: Apr. 11, 1977

Related U.S. Application Data

[62] Division of Ser. No. 585,898, Jun. 11, 1975, Pat. No. 4,034,101.

[30] Foreign Application Priority Data

Jun. 28, 1974 United Kingdom ............... 28722/74

[51] Int. Cl.$^2$ ................. C07D 277/22; A61K 31/425

[52] U.S. Cl. ............................... 424/270; 260/302 R; 260/302 H; 260/302 S; 260/302 A; 260/307 R; 260/307 H; 424/272

[58] Field of Search .......... 260/302 R, 302 H, 302 S, 260/302 A, 307 R, 307 H; 424/270, 272

[56] References Cited

U.S. PATENT DOCUMENTS 4,034,101  7/1977  Durant et al. .................... 424/270

*Primary Examiner*—R. Gallagher
*Attorney, Agent, or Firm*—Joan S. Keps; Richard D. Foggio; William H. Edgerton

[57] ABSTRACT

The compounds are N-oxy and N-amino guanidines which are histamine H$_2$-antagonists. A compound of this invention is N-hydroxy-N'-methyl-N"-[2-((4-methyl-5-imidazolyl)methylthio)ethyl]guanidine.

11 Claims, No Drawings

N-OXY AND N-AMINO GUANIDINES

This is a division of application Ser. No. 585,898 filed June 11, 1975, now U.S. Pat. No. 4,034,101.

This invention relates to pharmacologically active compounds, to pharmaceutical compositions comprising these compounds and to processes for their preparation. The compounds of the invention can exist as the addition salt but, for convenience, reference will be made throughout this specification to the parent compounds.

Many physiologically active substances elicit their biological actions by interaction with specific sites known as receptors. Histamine is such a substance and has a number of biological actions. Those biological actions of histamine which are inhibited by drugs commonly called "antihistamines" of which mepyramine is a typical example, and diphenhydramine and chlorpheniramine are other examples are mediated through histamine $H_1$-receptors (ash and (Ash *Brit. J. Pharmac. Chemother,* 27, 427, (1966)). However, other of the biological actions of histamine are not inhibited by 'antihistamines' and actions of this type which are inhibited by a compound described by Black et al. (Nature, 236, 385 (1972)) and called burimamide are mediated through receptors which are defined by Black et al. as histamine $H_2$-receptors. Thus histamine $H_2$-receptors may be defined as those histamine receptors which are not blocked by mepyramine but are blocked by burimamide. Compounds which block histamine $H_2$-receptors are referred to as histamine $H_2$-antagonists.

Blockade of histamine $H_2$-receptors is of utility in inhibiting the biological actions of histamine which are not inhibited by "antihistamines". Histamine $H_2$-antagonists are therefore useful, for example, as inhibitors of gastric acid secretion, as anti-inflammatory agents and as agents which act on the cardiovascular system, for example as inhibitors of the effects of histamine on blood pressure, in the treatment of certain conditions, for example inflammation and in inhibiting the actions of histamine on blood pressure, a combination of histamine $H_1$- and $H_2$-antagonists is useful.

The compounds with which the present invention is concerned are histamine $H_2$-antagonists. The compounds may be represented by the following general formula:

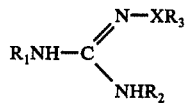

FORMULA I wherein $R_1$ represents a grouping of the structure shown in Formula II:

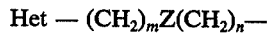

FORMULA II wherein Het is a nitrogen-containing 5 or 6 membered heterocyclic ring such as imidazole, pyridine, thiazole, isothiazole, oxazole, isoxazole, triazole or thiadiazole, which is optionally substituted by lower alkyl, hydroxyl, chlorine, bromine or amino; Z is sulphur or a methylene group; $m$ is 0, 1 or 2 and $n$ is 2 or 3 provided that the sum of $m$ and $n$ is 3 or 4; $R_2$ is hydrogen, lower alkyl or a grouping of the structure shown in Formula II wherein Het, $m$, $n$ and Z are as defined above; X is oxygen or NH; and $R_3$ is hydrogen, lower alkyl, aryl such as phenyl or arylalkyl such as benzyl.

Throughout the present specification, by the term "lower alkyl" we mean an alkyl group containing from 1 to 4 carbon atoms.

It will be understood that the structure illustrated in Formula I is only one of several representations and that other tautomeric forms are also covered by the present invention.

In a preferred group of compounds X is oxygen, $R_3$ is hydrogen and $R_2$ is lower alkyl. In a further preferred group $R_2$ is the same as $R_1$. In both of these groups it is particularly preferred that $m$ should be 1 and $n$ should be 2; compounds wherein Z is sulphur are also preferred; it follows therefore that compounds wherein $R_1$ and/or $R_2$ are Het—$CH_2S$—$(CH_2)_2$ are an important part of the present invention. Het may particularly usefully be imidazole, thiazole, isothiazole or pyridine optionally substituted by methyl, hydroxyl, chlorine or bromine.

A useful series of compounds are those wherein $R_3$ is hydrogen.

Examples of specific compounds falling within the scope of the present invention are N-hydroxy-N'-methyl-N''-[2-((4-methyl-5-imidazolyl)methylthio)ethyl]-guanidine, N-hydroxy-N',N''-bis[2-((4-methyl-5-imidazolyl)methylthio)ethyl]guanidine, N-methoxy-N'-methyl-N''-[2-((4-methyl-5-imidazolyl)methylthio)ethyl]guanidine, N-methoxy-N',N''-bis[2-((4-methyl-5-imidazolyl)methylthio)ethyl]guanidine, N-amino-N'-methyl-N''-[2-((4-methyl-5-imidazolyl)methylthio)ethyl]guanidine, N-amino-N',N''-bis[2-((4-methyl-5-imidazolyl)methylthio)ethyl]guanidine and N-hydroxy-N'-methyl-N''-[2-((2-thiazolyl)methylthio)ethyl]guanidine.

A method which may be used for the production of compounds of Formula I commences from a thiourea of the Formula III:

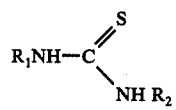

FORMULA III

Reaction of this compound with a lower alkyl halide of formula AY wherein A is lower alkyl and Y is halogen, e.g. methyl iodide or with lower alkanol of formula AOH in the presence of a halogen acid, HY, e.g., with methanolic hydrogen, chloride yields the isothiourea of Formula IV (shown as the acid addition salt):

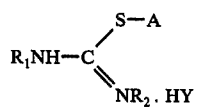

FORMULA IV wherein A, Y, $R_1$ and $R_2$ have the above mentioned significance. Treatment of this isothiourea with a compound of formula $R_3X\ NH_2$, wherein $R_3$ and X have the same significance as in Formula I, yields the compounds of Formula I. This latter reaction is preferably carried out in the presence of a base such as potassium bicarbonate.

An alternative method which may be used for the production of compounds of Formula I wherein X is NH consists of treating the isothiourea of Formula IV (shown as the acid addition salt) wherein A, Y, $R_1$ and $R_2$ have the above significance, with a compound of formula P₃ R₄ N.NH₂, wherein R₃ has the same significance as in Formula I and R₄ is a protecting group such as tert-butyloxycarbonyl. This reaction is preferably carried out in the presence of a base such as potassium bicarbonate. The protecting group is then removed with for example hydrochloric acid to yield the compounds of Formula I.

The thioureas of Formula III are prepared as follows:

Starting from an amine of Formula $R_1NH_2$, wherein $R_1$ has the same significance as in Formula I, reaction with carbon disulphide and a lower alkyl halide or sulphate such as methyl iodide or methyl sulphate gives the corresponding dithiocarbamic ester of Formula V (which will of course normally exist in the form of the acid addition salt).

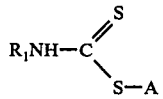

FORMULA V wherein A is lower alkyl and subsequent reaction of this compound under alkaline conditions (e.g. in the presence of sodium ethoxide in a solvent such as ethanol) with the amine of formula $R_2NH_2$, gives the required thiourea of Formula III. Where $R_1$ and $R_2$ are the same, the required compounds can be produced without isolation of an intermediate of Formula V by the reaction of carbon disulphide with an excess (two moles or more) of the amine of formula $R_1NH_2$, this reaction being conveniently carried out in a solvent such as ethanol.

The compounds of Formula I block histamine $H_2$-receptors, that is they inhibit the biological actions of histamine which are not inhibited by "antihistamines" such as mepyramine but are inhibited by burimamide. For example, the compounds of this invention have been found to inhibit histamine-stimulated secretion of gastric acid from the lumen-perfused stomachs of rats anaesthetized with urethane, at doses of from 0.5 to 256 micromoles per kilogram intravenously. This procedure is referred to in the above mentioned paper of Ash & Schild. The activity of these compounds as histamine $H_2$-antagonists is also demonstrated by their ability to inhibit other actions of histamine which, according to the above mentioned paper of Ash and Schild, are not mediated by histamine $H_1$-receptors. For example, they inhibit the actions of histamine on the isolated guinea pig atrium and isolated rat uterus.

The compounds of this invention inhibit the basal secretion of gastric acid and also that stimulated by pentagastrin or by food.

In addition, the compounds of this invention show anti-inflammatory activity in conventional tests such as the rat paw oedema test, where the oedema is induced by an irritant, the rat paw volume is reduced by subcutaneous injection of doses of a compound of Formula I. In a conventional test, such as the measurement of blood pressure in the anaesthetised cat, the action of the compounds of this invention in inhibiting the vasodilator action of histamine can also be demonstrated. The level of activity of the compounds of this invention is illustrated by the effective dose producing 50% inhibition of gastric acid secretion in the anaesthetized rat (which for many of the compounds of Formula I is from 1 to 10 micromoles per kilogram) and the dose producing 50% inhibition of histamine-induced tachycardia in the isolated guinea pig atrium.

For therapeutic use, the pharmacologically active compounds of the present invention will normally be administered as a pharmaceutical composition comprising as the or an essential active ingredient at least one such compound in the basic form or in the form of an addition salt with a pharmaceutically acceptable acid and in association with a pharmaceutical carrier therefor. Such addition salts include those with hydrochloric, hydrobromic, hydriodic, sulphuric and maleic acids and may conveniently be formed from the corresponding bases of Formula I by standard procedures, for example by treating the base with an acid in a lower alkanol or by the use of ion exchange resins to form the required salt either directly from the base or from a different addition salt.

Pharmaceutical compositions comprising a pharmaceutical carrier and a compound of Formula I or a pharmaceutically acceptable acid addition salt thereof and methods of blocking histamine $H_2$-receptors which comprise administering a compound of Formula I or a pharmaceutically acceptable acid addition salt thereof are also objects of this invention. The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like.

A wide variety of pharmaceutical forms can be employed. Thus, if a solid carrier is used, the preparation can be tableted, placed in a hard gelatin capsule in powder or pellet form, or in the form of a troche or lozenge. The amount of solid carrier will vary widely but preferably will be from about 25 mg to about 1 g. If a liquid carrier is used, the preparation may be in the form of a syrup, emulsion, soft gelatin capsule, sterile injectable liquid contained for example in an ampoule, or an aqueous or nonaqueous liquid suspension.

The pharmaceutical compositions are prepared by conventional techniques involving procedures such as mixing, granulating and compressing or dissolving the ingredients as appropriate to the desired preparation.

The active ingredient will be present in the compositions in an effective amount to block histamine $H_2$-receptors. The route of administration may be oral or parenteral.

Preferably, each dosage unit will contain the active ingredient in an amount of from about 50 mg to about 250 mg.

The active ingredient will preferably be administered one to six times per day. The daily dosage regimen will preferably be from about 150 mg to about 1500 mg.

Advantageously the composition will be made up in a dosage form appropriate to the desired mode of administraton for example as a tablet, capsule, injectable solution or as a cream or ointment for topical application.

The invention is illustrated but in no way limited by the following Examples in which all temperatures are in degrees Centigrade:

EXAMPLE I

N-Hydroxy-N'-methyl-N"-[2-((4-methyl-5-imidazolyl)-methylthio)ethyl]guanidine dihydrochloride (i) Dry hydrogen chloride gas was passed into a solution of N-methyl-N'-[2-((4-methyl-5-imidazolyl)methylthio)ethyl]thiourea (73.2 g) in methanol (600 ml) and the mixture was refluxed for 5 hours. Concentration and re-evaporation with isopropyl alcohol afforded a crystalline solid which was recrystallised from isopropyl alcohol-ether to give N,S-dimethyl-N'-[2-((4-methyl-5-imidazolyl)methylthio)ethyl]isothiourea dihydrochloride (96.2 g) m.p. 191°–192° (isopropyl alcohol-ether).

(ii) A mixture of the isothiourea dihydrochloride (3.3 g) hydroxylamine hydrochloride (2.1 g), potassium hydrogen carbonate (10 g) and anhydrous dimethyl formamide (50 ml) was vigorously stirred for 4 hours at 85°. Following cooling and filtration from inorganic material the filtrate was concentrated to yield the free base and this was then dissolved in N hydrochloric acid (40 ml) and ethanol (10 ml). Concentration and trituration of the residual oil with isopropanol afforded a solid which was recrystallised from aqueous isopropyl alcohol to give the title compound (0.85 g) m.p. 218°–219°.

When an aqueous ethanolic solution of this dihydrochloride is passed down a suitable ion-exchange column, for example of IRA-401 in basic form, the free base in pure form may be obtained by concentration of the eluate. Pretreatment of the column with an acid e.g., sulphuric acid leads to the production of the appropriate salt, e.g. the disulphate.

EXAMPLE 2

N-Hydroxy-N,N''-bis[2-((4-methyl-5-imidazolyl)methylthio)ethyl]guanidine trihydrochloride (i) A solution of 4-methyl-5-((2-aminoethyl)thiomethyl) imidazole (34.0 g) and carbon disulphide (7.6 g) in ethanol (250 ml) was heated under reflux for 6 hours. Concentration followed by chromatographic purification of the product on a column of silica gel with elution by isopropyl alcohol-ethyl acetate followed by isopropyl alcohol-ethanol gave N,N'-bis[2-(4-methyl-5-imidazolyl)methylthio)ethyl]thiourea (18 g), m.p. 133°–135°.

(Found: C, 47.0; H, 6.1; N, 22.0%. $C_{15}H_{24}N_6S_3$ requires: C, 46.8; H, 6.3; N, 21.9%).

(ii) The reaction of N,N'-bis-[2-((4-methyl-5-imidazolyl)methylthio)ethyl]thiourea (7.7 g) with ethanolic hydrogen chloride by the method described in Example 1 afforded S-methyl-N,N'-bis-[2-((4-methyl-5-imidazolyl)methylthio)ethyl]isothiourea trihydrochloride (9.0 g), m.p. 212°–215° (isopropyl alcohol).

Found: C, 37.6; H, 5.7; N, 16.3; S, 18.6; Cl, 20.5%. $C_{16}H_{26}N_6S_3$. 3 HCl requires: C, 37.8; H, 5.8; N, 16.5; S, 18.9; Cl, 20.9%.

(iii) A mixture of the isothiourea trihydrochloride (15.2 g) hydroxylamine hydrochloride (7.0 g) potassium hydrogen carbonate (16.0 g) and anhydrous dimethyl formamide (150 ml) was stirred vigorously for 3 hours at 90°. Following cooling, filtration and concentration the resultant free base was purified on a column of silica gel by elution with chloroform-methanolic ammonia. After treatment with an excess of ethanolic hydrogen chloride, the residue was dissolved in isopropanol and crystallised to give the title compound (2.1 g) m.p. 224°–225°.

(Found: C, 36.3; H, 5.6; N, 19.7; Cl, 21.3; S, 12.7%. $C_{15}H_{25}N_7OS_2$. 3 HCl requires: C, 36.6; H, 5.7; N, 19.9; Cl, 21.6; S, 13.0%).

EXAMPLE 3

N-Methoxy-N'-methyl-N''-[2-((4-methyl-5-imidazolyl)methylthio)ethyl]guanidine dihydrochloride A mixture of the isothiourea dihydrochloride from Example I(i) (6.6 g), methoxyamine hydrochloride (5.0 g), potassium hydrogen carbonate (8.0 g) and water (60 ml) was refluxed for 24 hours. Following cooling, an excess of sodium chloride was added and the solution extracted with chloroform (5×100 ml). The chloroform extracts were concentrated to give the free base which was purified on a column of silica gel by elution with chloroform-methanolic ammonia. After treatment with an excess of ethanolic hydrogen chloride, the residue was triturated with acetonitrile to give the title compound (2.5 g), m.p. 182°–185°.

(Found: C, 35.8; H, 6.3; N, 21.2; Cl, 21.3; S, 9.5%. $C_{10}H_{19}N_5OS$. 2 HCl requires: C, 36.4; H, 6.4; N, 21.2; Cl, 21.5; S, 9.7%)

EXAMPLE 4

N-Methoxy-N',N''-bis[2-((4-methyl-5-imidazolyl)methylthio)ethyl]guanidine trihydrochloride A mixture of the isothiourea trihydrochloride from Example 2(ii) (5.1 g), methoxyamine hydrochloride (2.5 g), potassium hydrogen carbonate (5.0 g) and water (30 ml) was refluxed for 24 hydrochloric hours. The products were partitioned between N sodium hydroxide and n-butanol. The n-butanol solution was then extracted with N hydrochloride acid, and the extracts concentrated and dissolved in isopropanol. After filtration from inorganic material, the filtrate gave the title compound (0.6 g). When a solution in aqueous ethanol of this compound was eluted from an ion exchange column of IRA-401 in nitrate form, the corresponding trinitrate was obtained. n.m.r. spectrum ($D_2O$):

$\delta$ 2.38 (singlet), 6H, Imidazole — $\underline{CH_3}$
$\delta$ 2.85 (triplet, J=7$H_2$), 4H, S—$\underline{CH_2}$—$CH_2$
$\delta$ 3.53 (triplet, J=7$H_2$), 4H, N—$\underline{CH_2}$—$CH_2$
$\delta$ 3.83 (singlet), 3H, O—$\underline{CH_3}$
$\delta$ 3.97 (singlet), 4H, Imidazole — $\underline{CH_2}$ — S
$\delta$ 8.87 (singlet), 2H, Imidazole — $\underline{H}$

EXAMPLE 5

N-Amino-N'-methyl-N''-[2-((4-methyl-5-imidazolyl)methylthio)ethyl]guanidine dihydrochloride A mixture of the isothiourea dihydrochloride from Example 1(i) (8.3 g), hydrazine sulphate (4.1 g), potassium hydrogen carbonate (12.5 g) and anhydrous dimethyl formamide (100 ml) was stirred at 90° C for 3 hours. Following cooling and filtration from inorganic material, the filtrate containing the free base was treated with ethanolic hydrogen chloride. The residue was then triturated with isopropanol to give a solid which was recrystallised from aqueous isopropanol to give the title compound (1.94 g), m.p. 234°–235°.

(Found: C, 34.0; H, 6.4; N, 26.2; Cl, 22.2; S, 10.0%. $C_9H_{18}N_6S$. 2HCl requires: C, 34.3; H, 6.4; N, 26.7; Cl, 22.5; S, 10.2%).

EXAMPLE 6

N-Amino-N',N''-bis[2-((4-methyl-5-imidazolyl)methylthio)ethyl]guanidine trihydrochloride A mixture of the isothiourea trihydrochloride from Example 2(ii) (5.1 g), hydrazine sulphate (1.6 g), potassium hydrogen carbonate (7.0 g) and anhydrous dimethyl formamide (60 ml) was stirred at 70° for 3 hours. Following cooling and filtration the filtrate containing the free base was treated with an excess of ethanolic hydrogen chloride to give the title compound.

EXAMPLE 7

N-Hydroxy-N'-methyl-N"-[2-(2-thiazolylmethylthio)ethyl]guanidine dihydrochloride (i) Methyl iodide (5 ml) was added to a solution of N-methyl-N'-[2-(2-thiazolylmethylthio)ethyl]thiourea (4.7 g) in methanol (50 ml), and the mixture was refluxed for 10 minutes. The products were concentrated and treated with ion-exchange resin IRA-401 ($Cl^-$) followed by an excess of ethanolic hydrogen chloride. Concentration of this solution gave N,S-dimethyl-N'-[2-(2-thiazolylmethylthio)ethyl]isothiourea dihydrochloride (5.6 g).

(ii) A mixture of the isothiourea dihydrochloride (0.46 g), hydroxylamine hydrochloride (0.35 g), potassium hydrogen carbonate (1.5 g) and anhydrous dimethyl formamide (10 ml) was stirred at 90° for 4 hours. The products were partitioned between chloroform and water, the chloroform evaporated to yield the free base and this was treated with an excess of ethanolic hydrogen chloride. After concentration, the residue was triturated with isopropanol to give the title compound (0.10 g), m.p. 171°–174°. n.m.r. spectrum $^2H_6$ dimethyl sulphoxide:

δ 2.78 (doublet, J = 5H$_2$), 3H, NH—CH$_3$
δ 3.12 (multiplet), 2H, S—CH$_2$—CH$_2$
δ 3.49 (multiplet), 2H, N—CH$_2$—CH$_2$
δ 4.36 (singlet), 2H, Thiazole—CH$_2$—S
δ 7.90 (multiplet), 2H, Thiazole—2H
δ 7.98 (multiplet), 2H, —NH—CNOH—NH—
δ 9.24 (broad singlet), 1H, —O—H

EXAMPLE 8

N-Methyl-N'-methylamino-N"-[2-((4-methyl-5-imidazolyl)methylthio)ethyl]guanidine dihydrochloride A mixture of the isothiourea dihydrochloride of Example 1 (i) (6.7 g), N-methyl-N-tert-butoxycarbonylhydrazine sulphate (5.7 g), potassium hydrogen carbonate (10.0 g) and anhydrous dimethylformamide (80 ml) was stirred at 90° C for 3 hours. After cooling, filtration and concentration to yield the free base, this was heated under reflux with ethanolic hydrogen chloride. Concentration and trituration of the residual product yielded the title compound.

EXAMPLE 9

N-Methyl-N'-hydroxy-N"-[3-((4-methyl-5-imidazolyl)methylthio)propyl]guanidine dihydrochloride Reaction of N-methyl-N'-[3-((4-methyl-5-imidazolyl)methylthio)propyl]thiourea with methanolic hydrogen chloride by the method of Example 1(i) yielded N,S-dimethyl-N'-[3-((4-methyl-5-imidazolyl)methylthio)propyl]isothiourea dihydrochloride which on treatment with hydroxylamine by the procedure of Example 1(ii) gave the title product.

EXAMPLE 10

N-Methyl-N'-hydroxy-N"-[4-(4-imidazolyl)butyl]guanidine dihydrochloride

When N-methyl-N'-[4-(4-imidazolyl)butyl]thiourea is reacted with methanolic hydrogen chloride by the procedure of Example 1(i) the product is N,S-dimethyl-N'-[4-(4-imidazolyl)butyl]isothiourea which on treatment with hydroxylamine by the procedure of Example 1(ii) gives the title product.

EXAMPLE 11

N-Methyl-N'-hydroxy-N"-[4-(2-thiazolyl)butyl]guanidine disulphate

N-Methyl-N'-[4-(2-thiazolyl)butyl]thiourea was converted into its hydriodide salt with 66% hydriodic acid. This salt was dissolved in methanol, methyl iodide added and the solution heated under reflux for 2 hours. Concentration and crystallisation of the resultant oil gave N,S-dimethyl-N'-[4-(2-thiazolyl)butyl]isothiourea dihydriodide. Reaction of this isothiourea with hydroxylamine by the procedure of Example 1(ii) gave the title product.

EXAMPLE 12

N-Methyl-N'-hydroxy-N"-[2-((3-chloro-2-pyridyl)methylthio)ethyl]guanidine dinitrate By the procedure of Example 1(i), N-methyl-N'-[2-((3-chloro-2-pyridyl)methylthio)ethyl]thiourea was converted to N,S-dimethyl-N'-[2-((3-chloro-2-pyridyl)methylthio)ethyl]isothiourea dihydrochloride which, on reaction with hydroxylamine by the procedure of Example 1(ii) yielded the title product.

EXAMPLE 13

N-Methyl-N'-phenoxy-N"-[2-((4-methyl-5-imidazolyl)methylthio)ethyl]guanidine dihydrochloride Reaction of the isothiourea dihydrochloride produced by Example 1(i) with phenoxyamine by the procedure of Example 1(ii) gave the title product.

EXAMPLE 14

N-Methyl-N'-benzyloxy-N"-[2-((4-methyl-5-imidazolyl)methylthio)ethyl]guanidine dihydrochloride Reaction of the isothiourea dihydrochloride of Example 1(i) with benzyloxyamine by the procedure of Example 1(ii) gave the title product.

EXAMPLE 15

Reaction of the following isothiourea dihydrochlorides (prepared from the corresponding thioureas by the procedure of Example 1(i):

(a) N,S-dimethyl-N'-[2-((3-isothiazolyl)methylthio)ethyl]isothiourea dihydrochloride
(b) N,S-dimethyl-N'-[3-(2-oxazolyl)thiopropyl]isothiourea dihydrochloride
(c) N,S-dimethyl-N'-[2-((3-isoxazolyl)methylthio)ethyl]isothiourea dihydrochloride
(d) N,S-dimethyl-N'-[2-((3-1,2,4-triazolyl)methylthio)ethyl]isothiourea dihydrochloride
(e) N,S-dimethyl-N'-[2-((5-amino-2-1,3,4-thiadiazolyl)methylthio)ethyl]isothiourea dihydrochloride
(f) N,S-dimethyl-N'-[2-((3-hydroxy-2-pyridyl)methylthio)ethyl]isothiourea dihydrochloride
(g) N,S-dimethyl-N'-[2-((3-bromo-2-pyridyl)methylthio)ethyl]isothiourea dihydrochloride
(h) N,S-dimethyl-N'-[2-(2-(4-methyl-5-imidazolyl)ethylthio)ethyl]isothiourea dihydrochloride with hydroxylamine according to the procedure of Example 1(ii) yields the following products:

(a) N-hydroxy-N'-methyl-N''-[2-((3-isothiazolyl)methylthio)ethyl]guanidine dihydrochloride
(b) N-hydroxy-N'-methyl-N''-[3-((2-oxazolyl)thiopropyl]guanidine dihydrochloride
(c) N-hydroxy-N'-methyl-N''-[2-((3-isoxazolyl)methylthio)ethyl]guanidine dihydrochloride
(d) N-hydroxy-N'-methyl-N''-[2-((3-1,2,4-triazolyl)methylthio)ethyl]guanidine dihydrochloride
(e) N-hydroxy-N'-methyl-N''-[2-((5-amino-2-1,3,4-thiadiazolyl)methylthio)ethyl]guanidine dihydrochloride
(f) N-hydroxy-N'-methyl-N''-[2-((3-hydroxy-2-pyridyl)methylthio)ethyl]guanidine dihydrochloride
(g) N-hydroxy-N'-methyl-N''-[2-((3-bromo-2-pyridyl)methylthio)ethyl]guanidine dihydrochloride
(h) N-hydroxy-N'-methyl-N''-[2-(2-(4-methyl-5-imidazolyl)ethylthio)ethyl]guanidine dihydrochloride.

EXAMPLE 16

Reaction of the isothiourea dihydrochloride of Example 1(i) with n-propoxyamine and n-butyoxyamine according to the procedure of Example 1(ii) gave respectively N-methyl-N'-n-propoxy-N''-[2-((4-methyl-5-imidazolyl)methylthio)ethyl]guanidine dihydrochloride and N-methyl-N'-n-butoxy-N''-[2-((4-methyl-5-imidazolyl)methylthio)ethyl]guanidine dihydrochloride.

EXAMPLE 17

Reaction of the following isothiourea salts (prepared from the corresponding thioureas by the procedure of Example 1(i):

(a) S-methyl-N-[2-((4-methyl-5-imidazolyl)methylthio)ethyl]isothiourea dihydrochloride
(b) S-methyl-N-n-butyl-N'-[2-((4-methyl-5-imidazolyl)methylthio)ethyl]isothiourea dihydrochloride
(c) S-methyl-N-[2-((4-methyl-5-imidazolyl)methylthio)ethyl]-N'-[2-((2-thiazolyl)methylthio)ethyl]isothiourea trihydrochloride, with hydroxylamine according to the procedure of Example 1 (ii) yields the following products:

(a) N-hydroxy-N'-[2-((4-methyl-5-imidazolyl)methylthio)ethyl]guanidine dihydrochloride
(b) N-hydroxy-N'-n-butyl-N''-[2-((4-methyl-5-imidazolyl)methylthio)ethyl]guanidine dihydrochloride
(c) N-hydroxy-N'-[2-((4-methyl-5-imidazolyl)methylthio)ethyl]-N''-[2-(2-thiazolyl)methylthio)ethyl]guanidine trihydrochloride.

EXAMPLE 18

| Ingredients | Amounts |
|---|---|
| N-Hydroxy-N'-methyl-N''-[2-((4-methyl-5-imidazolyl)methylthio)ethyl]guanidine dihydrochloride. | 150 mg |
| Sucrose | 75 mg |
| Starch | 25 mg |
| Talc | 5 mg |
| Stearic Acid | 2 mg |

The ingredients are screened, mixed and filled into a hard gelatin capsule.

EXAMPLE 19

| Ingredients | Amounts |
|---|---|
| N-Hydroxy-N,N'-bis-[2-((4-methyl-5-imidazolyl)methylthio)ethyl]guanidine trihydrochloride | 200 mg. |
| Lactose | 100 mg. |

The ingredients are screened, mixed and filled into a hard gelatin capsule.

What we claim is:

1. A compound of the formula:

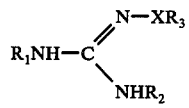

FORMULA I wherein $R_1$ represents a grouping of the structure shown in the formula:

FORMULA II wherein Het is thiazole, isothiazole, oxazole or isoxazole, which is optionally substituted by lower alkyl, chlorine or bromine; Z is sulphur or a methylene group; $m$ is 0, 1 or 2 and $n$ is 2 or 3 provided that the sum of $m$ and $n$ is 3 or 4; $R_2$ is hydrogen, lower alkyl or a grouping of the structure shown in Formula II wherein Het, $m$, $n$ and Z are as defined above; X is oxygen or when $R_2$ is a grouping of the structure shown in Formula II, X may be NH; and $R_3$ is hydrogen, lower alkyl, phenyl or benzyl, or a pharmaceutically acceptable acid addition salt thereof.

2. A compound of claim 1 wherein X is oxygen and $R_3$ is hydrogen.
3. A compound of claim 1 wherein $R_2$ is lower alkyl.
4. A compound of claim 1 wherein $R_2$ is the same as $R_1$.
5. A compound of claim 1 wherein $m$ is 1 and $n$ is 2.
6. A compound of claim 1 wherein Z is sulphur.
7. A compound of claim 1 wherein Het is thiazole or isothiazole optionally substituted by methyl, chlorine or bromine.
8. A compound of claim 1, said compound being N-hydroxy-N'-methyl-N''-[2-((2-thiazolyl)methylthio)ethyl]guanidine.
9. A pharmaceutical composition to block histamine $H_2$-receptors comprising a pharmaceutically acceptable diluent or carrier and, in an effective amount to block histamine $H_2$-receptors, a compound of claim 1.
10. A method of blocking histamine $H_2$-receptors which comprises administering to an animal in need of blocking of histamine $H_2$-receptors in an effective amount to block histamine $H_2$-receptors a compound of claim 1.
11. A method of inhibiting gastric acid secretion which comprises administering to an animal in need thereof in an effective amount to inhibit gastric acid secretion a compound of claim 1.

* * * * *

UNITED STATES PATENT AND TRADEMARK OFFICE
CERTIFICATE OF CORRECTION

PATENT NO. : 4,093,729

DATED : June 6, 1978

INVENTOR(S) : Graham John Durant, Charon Robin Ganellin and Geoffrey Robert Owen It is certified that error appears in the above–identified patent and that said Letters Patent are hereby corrected as shown below:

Column 1, line 21, "(ash and (Ash" should read -- (Ash and Schild, -- .

Signed and Sealed this

Seventh Day of November 1978

[SEAL]

Attest:

RUTH C. MASON
*Attesting Officer*

DONALD W. BANNER
*Commissioner of Patents and Trademarks*